US005976468A

United States Patent [19]

Godec et al.

[11] Patent Number: 5,976,468

[45] Date of Patent: Nov. 2, 1999

[54] APPARATUS AND METHOD TO SUPPLY A FLUID SAMPLE TO AN ANALYZER

[75] Inventors: Richard D. Godec, Longmont; Frank J. Silvester, Boulder; Blaine R. Bateman, Louisville, all of Colo.

[73] Assignee: Sievers Instruments, Inc., Boulder, Colo.

[21] Appl. No.: 09/191,610

[22] Filed: Nov. 13, 1998

Related U.S. Application Data

[63] Continuation of application No. 08/629,609, Apr. 9, 1996, Pat. No. 5,837,203.

[51] Int. Cl.$^{6}$ .......... G01N 1/10

[52] U.S. Cl. .......... 422/100; 422/63; 422/103; 436/52; 436/174; 436/180; 73/863.81; 73/864.34; 73/864.52; 73/864.74

[58] Field of Search .......... 422/62, 63, 81, 422/100, 102, 103, 104; 436/43, 52, 174, 179, 180; 73/863.81, 861.34, 864.34, 864.83, 864.52, 864.74

[56] References Cited

U.S. PATENT DOCUMENTS

| | | | |
|---|---|---|---|
| 2,452,224 | 10/1948 | Collet, Jr. . | |
| 4,018,089 | 4/1977 | Dzula et al. | 73/422 |
| 4,056,967 | 11/1977 | Roberts | 73/1 |
| 4,478,095 | 10/1984 | Bradley et al. | 73/864 |
| 4,512,203 | 4/1985 | Calame-Lonjean et al. | 73/863 |
| 4,545,497 | 10/1985 | Martha, Jr. | 215/253 |
| 4,624,150 | 11/1986 | Shimizu | 73/864.81 |
| 4,638,675 | 1/1987 | Sperinck et al. | 73/864.34 |
| 4,912,985 | 4/1990 | Daum et al. | 73/863.25 |
| 4,998,954 | 3/1991 | Burr | 73/863.58 |
| 5,038,623 | 8/1991 | Zeh | 73/863.83 |
| 5,132,094 | 7/1992 | Godec et al. | 422/68.1 |
| 5,195,325 | 3/1993 | Short et al. | 62/50.2 |
| 5,270,219 | 12/1993 | DeCastro et al. | 436/180 |
| 5,310,683 | 5/1994 | Godec et al. | 436/123 |
| 5,326,532 | 7/1994 | Taylor | 422/100 |
| 5,353,652 | 10/1994 | Houck | 73/864.34 |
| 5,380,486 | 1/1995 | Anami | 422/63 |
| 5,417,105 | 5/1995 | Martinez et al. | 73/40.7 |
| 5,443,991 | 8/1995 | Godec et al. | 436/145 |

OTHER PUBLICATIONS

Patent Abstracts of Japan, vol. 009, No. 068 (p–344), Mar. 28, 1985.

JP 59 202041 a (Doryodkro Kakunenryo Kaihatsu Jigyodan; Others: 01), Nov. 15, 1984.

*Primary Examiner*—Long V. Le
*Attorney, Agent, or Firm*—Lappin & Kusmer LLP

[57] ABSTRACT

Apparatus and methods for supplying a portion of a fluid stream and, alternately, a fluid of known composition and concentration to an analyzer are provided. The fluid stream is directed through a series of connected chambers formed in an integral housing. A sampling needle has an inlet in one of the chambers and an outlet in fluid communication with the analyzer. When desired, a tube or vial containing a known fluid may be inserted into a chamber containing the sampling needle, so that the known fluid will be supplied to the analyzer. A second needle provides ventilation to the vial to prevent the formation of a vacuum as the known fluid is drained from the vial.

28 Claims, 2 Drawing Sheets

APPARATUS AND METHOD TO SUPPLY A FLUID SAMPLE TO AN ANALYZER

CROSS-REFERENCE TO RELATED APPLICATIONS

This application is a continuation of U.S. application Ser. No. 08/629,609 filed Apr. 9, 1996, which became U.S. Pat. No. 5,837,203, issued Nov. 17, 1998.

FIELD OF THE INVENTION

The present invention relates to the field of chemical analysis, and more particularly to a method and a device that supplies a portion of fluid from a stream to a chemical analyzer and, when desired, supplies fluid of known chemical composition to the analyzer.

BACKGROUND OF THE INVENTION

Fluid analysis is used in a wide variety of research, manufacturing, waste disposal and other applications. Typically, the fluid is transported from one location to another in a fluid stream, and it is often desirable to analyze the contents of the stream. This may be done by taking a sample from the fluid stream at selected time intervals. However, the composition of the fluid stream may vary considerably between the sampling intervals, so that the samples may not accurately reflect the composition of the stream. Collecting samples from the stream is also physically complicated. It is therefore often preferred to link an analyzer in-line with the fluid stream. Generally, analyzers only need test a small fraction of the total quantity of a stream to function properly, so that the majority of the fluid stream may bypass the analyzer. Diverting a small fraction of a fluid stream to an analyzer without using extensive and complicated plumbing can be a considerable design challenge.

Along with the fluid stream, it is necessary to supply a known fluid sample to an analyzer from time to time to insure that the analyzer is functioning properly or to calibrate the analyzer. This is done by observing whether the analyzer correctly analyzes the known sample. If the analyzer does not correctly identity the known sample, then the analyzer must be calibrated until it is operating within desired parameters. Of course, if the known sample does not in fact contain the precise composition that it is believed to contain, the analyzer will be incorrectly tested and calibrated. Therefore, it is imperative that the known sample be delivered to the user in a controlled condition. An ideal method of ensuring this is for the known sample to be prepackaged in small containers such as vials in the controlled environment of a facility specializing in such matters. This is especially an issue in the pharmaceutical industry where regulations require the measurement of total organic carbon in waters for injection and purified waters at levels below 500 ppb. Standards with such low concentrations are difficult to produce without special laboratory equipment that isolates the standard from carbon that may be in the air, and the containers for such standards must be cleaned with special cleaning agents and rinse water with ultra-low carbon concentrations.

Supplying the known sample to the analyzer may complicate the process of analyzing the fluid stream. Analyzers, in general, have only one inlet, so that the known sample must somehow be substituted into and out of the fluid stream path when the analyzer is tested. The prior art method of performing this swapping involves a multitude of discrete steps, many of which require plumbing changes and special tools. First, the fluid stream must be disconnected from the analyzer. Next, the known sample must be connected to the analyzer. After the analyzer is tested and calibrated, the known sample must be disconnected from the analyzer, and the fluid stream must be reconnected. Depending on the application, the process of connecting and disconnecting the fluid stream and the known sample may need to be repeated many times over relatively short time frames, such as days or weeks. As well as requiring much time from the operating personnel, the process causes substantial down time to the flow of the fluid stream, which may interfere with the manufacturing, disposal or other operations involving the fluid stream. The connecting and disconnecting process causes substantial wear on the involved parts, and hence reduces their reliability and operating life. A mistake in this process may allow fluid to leak from the fluid stream or the analyzer, perhaps endangering the health of persons exposed to the leaked fluid and certainly disrupting whatever downstream applications are in use. The use of valving or tubing sections that are unique to either the known sample or to the fluid stream adds complexity and moving parts, and invites contamination that can produce inaccurate or imprecise results. In the case of the fluid stream, this contamination can lead to the disruption of the downstream application of the fluid stream, potentially fouling manufacturing or treatment equipment. In the case of the known sample, contamination will result in an inaccurate sample being supplied to the analyzer, resulting in the analyzer being improperly tested and calibrated. When the fluid stream is once again connected to the analyzer, it may be erroneously analyzed by the improperly calibrated analyzer.

The above complications may prevent fluid stream operators from testing and calibrating an analyzer as often as may be optimally desired, or even to entirely forgo testing and calibrating the analyzer on any sort of a regular basis whatsoever. Simplifying the method of diverting a portion of a fluid stream supplying a known sample to an analyzer would therefore greatly improve the ease and efficacy of fluid stream testing. It is also very desirable that the apparatus be capable of operating at low flow rates. Thus, the interior dimensions of the apparatus should be small, to allow low flow rates while still ensuring rapid response times.

One approach to the problem is to maintain a store of known samples for calibration purposes inside the apparatus. The known sample would then be drawn upon each time the apparatus is calibrated by means of suitable switching and valving. A major drawback to that approach, however, is that many samples are not stable over time; therefore, the sample being used for calibration could have deteriorated at the time of the calibration in a manner that produces an erroneous calibration. Further, many samples used for calibration cannot be stored indefinitely within the apparatus due to safety concerns or, especially with respect to low level samples, contamination concerns.

Examples of compounds that are often tested for in fluids are those containing sulfur, nitrogen, and organic and inorganic carbon. For instance, a carbon detector that may benefit from the present invention is described is U.S. Pat. Nos. 5,443,991 and 5,132,094 to Godec et al. and assigned to the assignee of the present invention. Such detectors measure total organic carbon concentration (TOC) and total carbon concentration in water, a standard method for assessing the level of contamination of organic compounds in potable waters, industrial process waters, and municipal and industrial waste waters. TOC measurement is used to determine the purity of potable and process water for manned space based systems such as the space shuttle, and will in all likelihood be used in future manned explorations. A detector according to an embodiment of the above mentioned patents includes an acidification module, an inorganic carbon removal module incorporating a gas permeable membrane, and an oxidation reaction system. Coupled with an oxidation reactor to form carbon dioxide and a high sensitivity conductomeric detector, such a detector allows on-line measurements of the TOC of aqueous streams. Other carbon detection systems suitable to analyze aqueous streams use IR spectroscopy instead of conductomeric techniques.

A process for determining sulfur containing compounds (as well as other compounds) in a fluid stream is described in U.S. Pat. No. 5,310,683 to Godec et al. and assigned to the assignee of the present invention. Sulfur detection is used in diverse industries such as petrochemical refining, beer brewing and other consumer product manufacturing. In consumer products, trace levels of sulfur-containing compounds can impart an objectionable taste and odor. In petrochemical applications, trace sulfur contaminants can poison catalysts, damaging or destroying processing equipment. Constant and accurate monitoring of fluid streams in these processes is therefore an economic necessity. The method described in the above patent involves combusting a sample in a hydrogen/air flame of a flame ionization detector, and measuring the ionic species produced in the flame. Concurrently, sulfur monoxide produced in the flame is withdrawn and measured by ozone-induced chemiluminescence. Both sulfur monoxide, from which sulfur containing species are measured, and ions containing carbon, from which organic compound concentrations can be deduced, are formed in one detection operation.

The above analyzers are representative of the broad class of analyzers used to monitor fluid streams. The present invention has application with a wide variety of other analyzers designed to detect and measure many different compounds.

SUMMARY OF THE INVENTION

The present invention is a device and method that allows a portion of a stream of fluid to be diverted to an analyzer and also allows for a known fluid sample to be supplied to the analyzer so that the analyzer may be properly calibrated. In general, only a small portion of a fluid stream need be supplied to an analyzer; the remainder of the fluid stream may bypass the analyzer. After a portion of the fluid stream has been analyzed, it may be rejoined with the primary fluid flow path. Since a portion of the fluid stream is continuously diverted to the analyzer, the analyzer may continuously monitor the composition of the fluid flow instead of relying on intermittent samples.

The analyzer may receive a known fluid sample instead of a portion of the fluid stream when desired by a user. A vial or other container of the known sample may be placed in fluid communication with the analyzer, temporarily replacing the fluid stream. This may be done without disturbing the communication path between the analyzer and the fluid flow path, although the actual flow of the fluid stream is preferably halted. The known sample occupies the portion of the fluid flow path from which fluid is diverted to the analyzer so that the known sample, instead of fluid from the fluid stream, is then supplied to the analyzer. After the analyzer is tested and, if necessary, calibrated using the known sample, the container of known fluid sample may be removed, and the flow of the fluid stream may be resumed. Thus, the fluid stream and the known sample may be alternately supplied to the analyzer, without changing the connections leading to the analyzer or the fluid flow path. Also, the known sample may be supplied to the analyzer in a controlled condition, as the container of fluid may remain hermetically sealed until it is coupled with the analyzer. The known sample can be introduced for calibration of the device, and then removed for use of the device with a sample stream, without the use of any special tools and without any changes in the general plumbing of the system. There are no moving parts in the apparatus, and no valving or tubing sections which are unique to the known sample or to the fluid stream which could become contaminated to distort the analysis.

Preferred embodiments of the invention include several additional features. An overflow port allows fluid to escape from the device if the fluid pressure exceeds a threshold level, thereby reducing the fluid pressure and possibly preventing damage to the device or to downstream applications. The invention may supply air to the container containing the known fluid sample as fluid drains from the container to the analyzer, so that a vacuum is prevented from forming in the container. The invention may be formed in a compact, integral unit, that allows for easy installation into a fluid flow path and that may be safely used with a wide range of fluids, even many corrosive fluids, over a wide temperature range.

In a preferred embodiment, the fluid stream is directed from an external conduit into a housing having an inlet and an outlet. The fluid stream is first directed into a sampling chamber on one side of the housing. The sampling chamber extends to an opening at the top of the block, through which a tube containing a known sample may be inserted. When the fluid stream is directed through the housing, this tube opening is sealed by a housing cover. The sampling chamber leads to a horizontal weir that extends beneath the top of the housing, through which the fluid stream flows. The horizontal weir leads to a discharge chamber, which extends parallel to the sampling chamber towards an outlet at the bottom of the housing. An external conduit leads from the outlet to any desired location, such as downstream manufacturing equipment or a disposal reservoir.

A portion of the fluid stream is diverted from the primary fluid stream to the analyzer through a conduit, such as a needle, positioned in the sampling chamber. As the fluid stream flows through the sampling chamber, some of the fluid will be drawn through the needle. The needle extends through the bottom of the sampling chamber and is in fluid communication with an outlet in the bottom of the housing. The analyzer is coupled to this outlet, either directly or through a conduit.

The present invention also provides a convenient method to supply a standardized fluid sample of known composition and concentration to the analyzer when desired, so that the proper operation of the analyzer may be verified and, if necessary, calibrated. The known sample is preferably supplied in a vial similar in size to a standard laboratory test tube, with the mouth of the vial sealed by an inert frangible diaphragm such as a teflon lined silicone disk. This allows the sample to be manufactured and transported to the eventual user in a clean or sterile condition. To supply the known sample to the analyzer, the housing cover is removed, exposing the vial receptacle located above the sampling chamber.

The vial is then inserted into the sampling chamber, with the mouth positioned downward. The diaphragm is first punctured by a hollow venting conduit, preferably a needle, that extends upwards in the sampling chamber parallel to, and somewhat higher than, the sampling needle. As the vial is slid down into the sampling chamber, the diaphragm is next punctured by the sampling needle. The known fluid sample in the vial is then transported through the sampling needle to the analyzer, allowing for proper calibration.

As fluid is transported from the vial to the analyzer, air (or some other substance) must flow into the vial to prevent a vacuum from forming therein. This is preferably accomplished through the venting needle. The end of the venting needle that punctures the diaphragm is situated in the vial. The other end of the venting needle communicates with the atmosphere (or possibly another pressurized or unpressurized gaseous source), preferably by extending into a venting chamber located beneath the sampling chamber. The venting chamber is in fluid communication with the sampling chamber via the venting needle, but is otherwise fluidly sealed therefrom so that the primary fluid flow path from the sampling chamber to the horizontal weir is not substantially disturbed. The venting chamber is also in gaseous communication with the discharge chamber, through a conduit that, preferably, extends externally from the housing. Air is then supplied through the conduit and the venting chamber into the vial to replace the volume of fluid supplied to the analyzer. It should be appreciated that air could be supplied to the vial from locations other than the discharge chamber. For instance, the venting chamber could have a conduit leading externally from the housing to other destinations in addition to or instead of the conduit leading to the discharge chamber.

When the device is operating with the fluid stream flowing through the chambers, a portion of the fluid stream may flow through the venting needle and assists in cleaning it. Since the venting needle is linked with the discharge chamber, this causes no problem, as the fluid flowing through the venting needle merges with the remainder of the fluid in the discharge chamber. The external conduit linking the venting chamber and the discharge chamber may be removed and cleaned when necessary. In an alternate design, the venting chamber and the discharge chamber are linked by an internal conduit (i.e., a conduit contained fully within the housing), which allows for a somewhat more compact device, but complicates cleaning.

The vials of known sample may be suitable for one use or for multiple uses. A suitably elastomeric diaphragm will automatically seal after the vial is withdrawn from the housing, when the needles no longer penetrate the diaphragm. This allows the vial to be reused as long as sufficient fluid remains in the vial to test and calibrate the analyzer. Alternatively, the vials may be designed for one use, which has the advantages of a reduced risk of contamination and insuring that a sufficient amount of known sample fluid will be supplied to the analyzer.

After the analyzer has been tested and calibrated, the vial may be removed and stored for another use, or may be discarded or perhaps refilled. The fluid stream through the housing may then be resumed. When desired, the known sample may again be supplied to test and calibrate the analyzer.

In a preferred embodiment of the invention, the overflow port is located above the horizontal weir where the horizontal weir joins the discharge chamber. During normal flow, the fluid stream will not exit the device through the overflow port, as it is located above the horizontal weir. Should the pressure on the device increase beyond a threshold level, however, the overflow port will allow a portion of the fluid stream to be discharged and the pressure through the device to be reduced.

The housing may be manufactured of any substance able to withstand high temperatures and a variety of corrosive fluids. In the pharmaceutical industry, for example, fluid temperatures may reach 99° C. The housing material should thus be capable of withstanding such temperatures without introducing contaminants from the material into the fluid stream. Polysulfone is a preferred material, because of its excellent resistance to heat and corrosion and because it may be molded and machined to the desired shape. Also, polysulfone is at least semi-transparent, which allows a user to observe the flow of fluid through the device, and detect any blockages, leaks, or other operational disruptions. Other materials may also be suitable.

The interior dimensions of the flow paths are very small. This allows for rapid response times even at very low flow rates, as low as about 10 ml/min in a preferred embodiment (although still lower flow rates could be achieved if desired by further miniaturization of the flow paths).

In light of the above description and the more detailed description that follows, it may thus be appreciated that the invention provides for a convenient method of diverting a portion of a fluid stream to an analyzer, and alternately supplying a known fluid sample to the analyzer. The invention uses a minimum of components and may be used with a wide variety of fluids and analyzers.

DETAILED DESCRIPTION OF THE INVENTION

Figure 1:
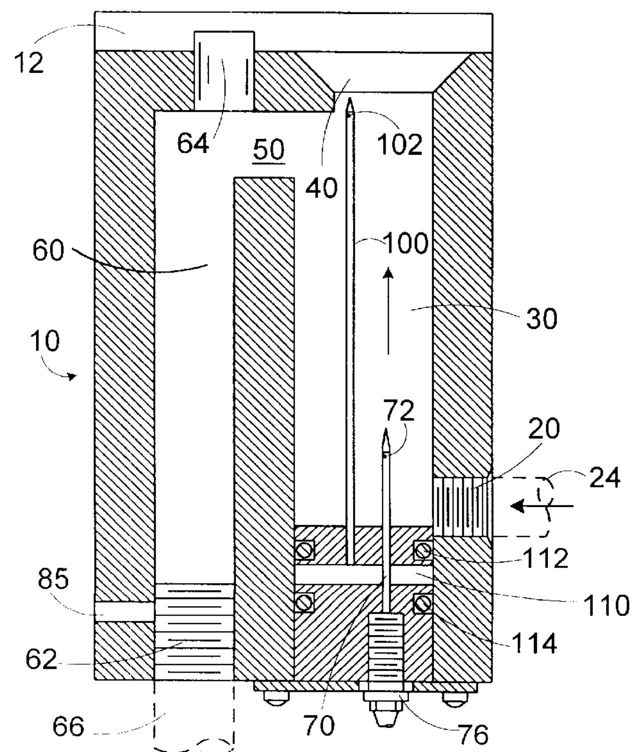
FIG. 1 is an elevation view of an embodiment of the present invention.

Referring to FIG. 1, the present invention in a preferred embodiment includes an integrated rectangular housing 10 having a fluid inlet 20 through which fluid may be introduced from an exterior intake conduit 24. The inlet 20 leads to a sampling chamber 30 that extends through the housing 10 substantially along one side of the housing 10. The sampling chamber 30 continues towards the top of the housing 10 to a vial receptacle 40 that leads to the housing 10 exterior. Beneath the vial receptacle 40, a horizontal weir 50 runs perpendicular from the sampling chamber 30. The horizontal weir 50 extends towards the opposite side of the housing 10 from the sampling chamber 30, and connects to a discharge chamber 60. The discharge chamber 60 runs parallel to the sampling chamber 30, and terminates at the bottom of the housing 10 at a discharge outlet 62 and terminates at the top of the housing 10 at an overflow outlet 64. An external discharge conduit 66 may be attached to the discharge outlet 62. In an alternative embodiment, there is no discharge chamber, but the discharge outlet is directly in the sampling chamber 30.

While the housing 10 is preferably an integrated unit, the above described chambers could be formed from either a singe piece of conduit or from separate conduits joined together. However, the integrated unit, in which the separate chambers are bored through an otherwise substantially solid piece of material, provides strong and leak-proof chambers. The rectangular shape of the housing 10 may modified to almost any shape whatsoever. A rectangular shape is generally preferred as it efficiently uses space and allows for the housing 10 to be mounted to any flat surface.

A housing cover 12 is removably attached to the top of the housing 10, and covers the vial receptacle 40. The housing cover 12 partially covers the overflow outlet 64, so that the overflow outlet 64 is covered from above by the housing cover 12 but is open at a side at the interface between the housing 10 and the housing cover 12. With the housing cover 12 placed on the housing 10, fluid may flow through the housing 10 in a circuit starting at the inlet 20, through the sampling chamber 30, across the horizontal weir 50, and through the discharge chamber 60 to the discharge outlet 62 and discharge conduit 66. The fluid stream will not normally be at sufficient pressure to exit the housing 10 through the overflow outlet 64; however, the overflow outlet 64 will allow fluid to escape should the pressure reach a predetermined threshold level.

Figure 2:
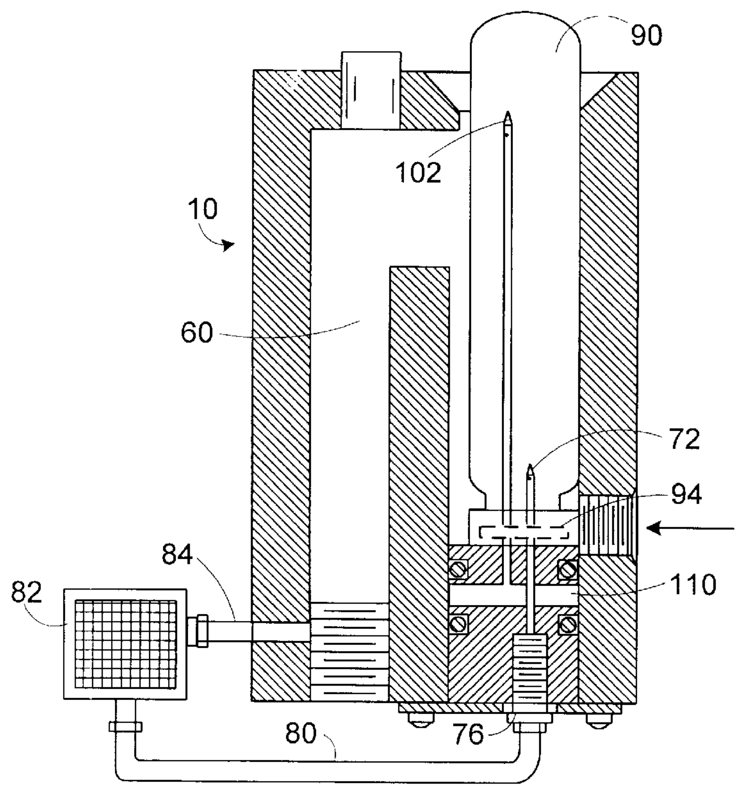
FIG. 2 is an elevation view of an embodiment of the present invention, as it supplies fluid from an inserted vial to an analyzer.

A conduit, preferably a hollow sampling needle 70, is positioned within the sampling chamber 30, with an inlet 72 proximate the top of the needle 70. Preferably, the inlet 72 is positioned so as to pierce the septum. The sampling needle 70 continues beneath the sampling chamber 30 to the bottom of the housing 10, where the sampling needle 70 terminates at a sampling outlet 76. Referring to FIG. 2, a sampling conduit 80 may be connected to the sampling outlet 76, and may run to a chemical analyzer 82 or other desired sampling apparatus. Alternatively, depending on the analyzer 82, the analyzer 82 may be directly connected to the sampling outlet 76. In either case, when fluid is flowing through the housing 10 from the inlet 20 to the outlet 62, an amount of fluid will be diverted through the sampling needle 70 to the analyzer 82. The amount of fluid diverted will typically be a small fraction of the total amount of fluid entering the inlet 20.

The analyzer 82 preferably contains a discharge conduit 84 in fluid communication with the discharge chamber 60 via an analyzer waste inlet 85, so that all of the fluid will be commingled for manufacturing use, disposal, or other downstream application. Otherwise, a separate disposal system would be necessary for the fluid supplied to the analyzer 82, requiring redundant conduits and storage receptacles. In some applications, however, the analyzer 82 may alter the fluid during the analyzing process, and it may not be desirable to reintroduce that fluid into the primary fluid stream that is not diverted to the analyzer 82. Of course, a separate disposal system may be attached to the analyzer 82 in such situations.

Interposed within a fluid stream as described above, the present invention allows for a constant sample of the fluid stream to be analyzed with minimal disruption to the primary stream flow. The constant flow to the analyzer 82 allows for the contents of the fluid stream to be analyzed as often as desired, such as on a periodic basis, or even continuously, as determined by the operation of the analyzer 82.

The present invention also allows for a sample of known chemical composition and concentration to be supplied to the analyzer 82. This is useful so that the integrity of the analyzer 82 may be monitored by verifying that the known chemical is correctly analyzed. If the analyzer 82 analyzes the known chemical sample within acceptable limits, the normal fluid stream flow through the inlet 20 may be resumed. If the analyzer 82 does not analyze the known sample within acceptable limits, the analyzer 82 may be calibrated until the known chemical is correctly analyzed. The fluid stream is analyzed, and a known sample is analyzed, without changes to the plumbing configuration or the need for any tools to accomplish the change, and without employing any moving parts. Also, the configuration of the device ensures that the known sample passes through the same inlets and conduits as the fluid stream, thereby avoiding the inaccuracy and imprecision that can result from valves or tubing sections which are unique to the known sample or to the fluid stream.

Figure 3:
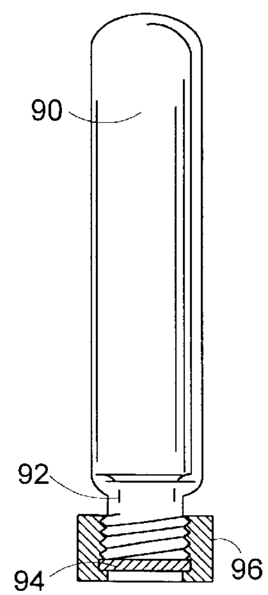
FIG. 3 is an elevation view of the vial of FIG. 2 with portions around the mouth of the vial cut away.

Referring to FIGS. 2 and 3, the known chemical is preferably supplied in a sealed vial 90 that may be inserted into the sampling chamber 30 through the vial receptacle 40. To access the vial receptacle 40, the housing cover 12 must be opened, exposing the vial receptacle 40. The vial 90 is preferably cylindrical and dimensioned similarly to a typical chemical test tube. The mouth 92 of the vial 90 is sealingly covered by an inert frangible elastomeric diaphragm 94. The diaphragm 94 may be made of silicone or other materials, and may be secured to the vial 90 by a screw cap 96 that screws around the exterior of the mouth 92. The diaphragm 94 allows a fluid sample of known composition and concentration to be supplied to a user in a controlled condition.

To supply fluid from the vial 90 to the analyzer 82, the tube 90 is inserted into the sampling chamber 30 with the mouth 92 end downward. The diaphragm 94 is punctured by a venting needle 100 located in the sampling chamber 30 parallel to the sampling needle 70 and extending higher in the sampling chamber 30 than does the sampling needle 70. As the vial 90 is further inserted into the sampling chamber 30, the diaphragm is punctured by the sampling needle 70. The vial 90 may be inserted until the screw cap 96 seats onto the bottom of the sampling chamber 30.

Once the diaphragm 94 is punctured by the sampling needle 70, the known chemical contained within the vial 90 will be supplied to the analyzer 82 by the sampling needle 70, and the analyzer 82 may then be calibrated as necessary. The purpose of the venting needle 100 is to supply air to the vial 90 to prevent the formation of a vacuum in the vial 90 as fluid drains out of the vial 90. Otherwise, the negative pressure created by the vacuum that would form in the end of the vial 90 opposite the mouth 92 would disrupt the smooth fluid flow from the vial 90. Air or other gas is supplied into the vial 90 through the venting needle 100 at a venting needle inlet 102 located proximate the end of the venting needle 100 that extends above the sampling chamber 30. In an alternative embodiment, the venting needle 100 extends out the bottom of the housing and is connected via a conduit to the discharge chamber 60 or to other replacement fluid sources.

The end of the venting needle 100 opposite the venting needle inlet 102 extends into a venting chamber 110 located beneath the sampling chamber 30. The venting chamber 110 is sealed from the sampling chamber 30 by the bottom of the sampling chamber 30, and preferably also by an 0-ring 112 disposed at the top of the venting chamber 110. The bottom of the venting chamber 110 preferably is sealed by an 0-ring 114. The venting chamber 110 is in fluid communication with the discharge chamber 60 via a venting conduit 116 (see FIG. 4). When the fluid stream is disrupted at inlet 20, the discharge chamber 60 will empty so that the discharge chamber 60 will contain air when the vial 90 is fitted into the sampling chamber 30.

Figure 4:
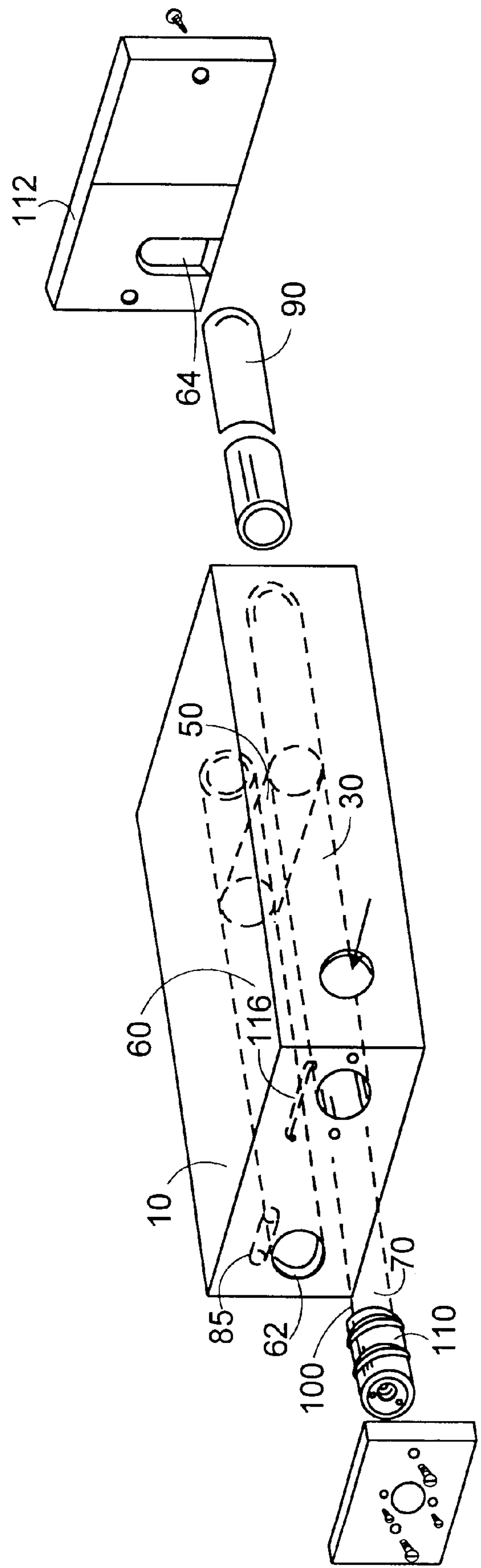
FIG. 4 is a partially exploded perspective view of an embodiment of the present invention, with interior portions shown in phantom.

When a fluid stream is flowing through the housing 10 via the inlet 20 (i.e., when the vial 90 is not in use), a small portion of the fluid stream may flow through the venting needle 100. This fluid will flow through the venting chamber 110 and the external venting conduit 116 back into the discharge chamber 60, where it will rejoin the primary fluid flow that reaches the discharge chamber 60 after flowing through the horizontal weir 50. In a preferred embodiment as shown in FIG. 4, the venting conduit 116 exits the housing 10 at the ventilation chamber 110 and re-enters the housing 10 at the discharge chamber 60. This allows the venting conduit 116 to be accessed for cleaning, when necessary. An alternative design is to rout the venting conduit 116 directly through the housing 10 between the venting chamber 110 and the discharge chamber 60, which provides a slimmer device profile and reduces the likelihood of the conduit being accidently severed.

The known sample may be supplied to the analyzer through methods other than the above-described vial and needle combination. For instance, a Luer fitting could be placed on the fluid sample container to mate with another Luer fitting on conduit placed in fluid communication with the analyzer 82. The known sample could be forced from its container by a syringe type pump, that avoids the creation of a vacuum by simultaneously forcing fluid from the container and reducing the volume of the container. Or, the known sample could be placed in a container similar to the vial 90 that has an opening on the end opposite its mouth, so air may be enter directly enter the container. This, however, may provide a less durable container than the described vial 90. The preferred embodiment that uses the vial 90 and venting and sampling needles 100 and 70 requires no moving parts, is reliable, and potentially allows reuse of the vial 90. After the vial 90 has been used, it may be removed from the housing 10 and the fluid stream may be resumed through the inlet 20. When desired, the same vial 90 or another similar vial may be used to again test and calibrate the analyzer 82. The sealed disposable tubes allow for known chemical samples to be supplied to the analyzer 82 as often as desired.

The housing 10 is preferably manufactured of polysulfone. The temperature, corrosion resistance and low extractables nature of polysulfone allows use with a wide variety of fluids transported over a broad temperature range without contamination of the sample, and polysulfone may be easily molded and machined into the desired shape. Other temperature and corrosion resistant materials, such as stainless steel, may also provide good results. However, polysulfone has the advantage of being at least semi-transparent, so that a user may observe the fluid flow through the housing 10 and take corrective action if any obstructions or other problems are detected. The small interior dimensions of the flow path in the preferred embodiment allows for quick analyzer response at flow rates as low as 10 ml/min or less.

While a preferred embodiment of the invention has been described, it should be appreciated that many modifications could be made that would not significantly affect the invention's functionality. For example, the directions of the relative chambers could be altered with respect to one another, such as by gently curving from one to another. As another example, several chambers could potentially be combined, such as the ventilation chamber 110 and the discharge chamber 60.

To use the invention to supply a portion of a fluid stream to the analyzer 82 and, alternately, to supply a known fluid sample to the analyzer 82, the following steps are performed. The analyzer 82 is connected to the housing 10, via the sampling conduit 80 attached to the sampling outlet 76, or, depending on the design of the analyzer 82, the analyzer 82 may be directly connected to the sampling outlet 76. The analyzer outlet 84 is attached to the discharge chamber 60 via the waste inlet 85 or, if it is desired to keep the analyzer 86 output effluent separated from the fluid flow stream, the analyzer 86 output may be separately disposed. The housing 10 is interposed into the fluid stream that is to be analyzed by connecting the fluid stream to the inlet 20. Fluid will then flow through the housing 10 through the sampling chamber 30, horizontal weir 50, discharge chamber 60, and the outlet 62.

A portion of the fluid flowing through the sampling chamber will be directed through the sampling needle 70 to the analyzer 82, so that the contents of the fluid stream may be analyzed. The fluid stream may be maintained in this flow pattern for as long a period of time as is desired by a user. If the pressure of fluid flowing through the housing 10 exceeds a threshold value, some of the fluid may flow through the overflow outlet 64, thereby releasing the excess pressure. A drainage conduit or reservoir (not shown) may be attached to the overflow port 64 so that the fluid is contained in the event that the overflow port 64 is used.

When desired, a sample of known concentration instead of the fluid stream may supplied to the analyzer 82. The housing 10 will be substantially drained of fluid through the discharge outlet 64. The housing cover 12 is then opened to expose the vial receptacle 40, and the vial 90 containing a known sample is inserted into the vial receptacle 40, with the mouth 92 of the vial inserted first until the vial cap 96 is seated on the bottom of the sampling chamber 30. The diaphragm 94 is twice punctured as it is inserted, first by the venting needle 100 and then by the sampling needle 70. During the vial 90 insertion process, some of the fluid contained in the vial 90 may leak through the venting needle to the discharge chamber 60. Because of the preferably small size of the venting needle inlet 102, this amount of fluid will be small and the leakage will be inconsequential.

After the vial 90 is fully inserted in the sampling chamber 90, the fluid contained in the vial 90 is supplied to the analyzer 82 through the sampling needle 70. As described above, the venting needle 100 supplies air to the vial to replace the volume of fluid drained therefrom, so that flow of fluid from the vial 90 to the analyzer 80 is smooth. After the analyzer 82 has received a sufficient amount of fluid from the vial 90 to be tested and calibrated, the vial 90 may be withdrawn from the sampling chamber 30. Optionally, the user may retain the vial 90 for further use, or may discard the vial 90 and select a new equivalent vial for the next testing and calibrating phase.

The housing cover 12 may be closed to seal the vial receptacle 40. The above steps may be repeated when it is next determined to test and calibrate the analyzer. It should be understood that certain obvious operational modifications may be required when alternate embodiments of the invention are utilized. The basic procedure of connecting the invention in-line with a fluid path and connecting an analyzer in fluid communication with the analyzer, and inserting a container of known fluid sample in fluid communication with the analyzer when desired, remains unchanged.

What is claimed is:

1. Analysis apparatus for analyzing a fluid in a fluid stream flowing between a fluid inlet and a drain, said apparatus comprising:

(a) a header assembly adjacent to a fluid region defined in part by said header assembly, said header assembly including an input port fluidically coupled to said fluid inlet, to said fluid region, and to an output port, the output port being defined by a first needle having a hollow interior, an inlet end in said fluid region, and an outlet end external to said fluid region; and, (b) an analyzer linked in-line with said fluid stream, said analyzer including an analyzer inlet fluidically coupled to said outlet end of said first needle and an analyzer outlet fluidically coupled to said drain, whereby an analysis fluid flow path is defined from said fluid inlet seriatim through said input port, a portion of said fluid region, said inlet end of said first needle, said hollow interior of said first needle, said outlet end of said first needle, said analyzer inlet, said analyzer, said analyzer outlet, to said drain.

2. Analysis apparatus according to claim 1 wherein said analyzer comprises a carbon detector for measuring the total carbon and total organic carbon concentration in said fluid stream.

3. Analysis apparatus according to claim 1 further comprising an alternative fluid flow path between said fluid inlet and said drain, said alternative fluid flow path including at least a portion of said fluid region and not including said analyzer.

4. Analysis apparatus according to claim 1 further wherein said header assembly includes a coupler adapted to receive a calibration vessel without moving said header assembly, said calibration vessel defining an interior chamber having a calibration port spanned by a pierceable membrane, whereby said inlet end of said first needle pierces said membrane and extends into said interior chamber when the calibration vessel is received by said coupler so as to establish a calibration fluid flow path from said interior chamber seriatim through said inlet end of said first needle, said hollow interior of said first needle, said outlet end of said first needle, said analyzer inlet, said analyzer, said analyzer outlet, to said drain.

5. Analysis apparatus according to claim 1 further comprising a venting fluid conduit extending between a source of venting fluid and said fluid region.

6. Analysis apparatus according to claim 4 further comprising a venting fluid conduit extending between a source of venting fluid and said interior chamber when said coupler receives said calibration vessel.

7. Analysis apparatus according to claim 4 further comprising: an alternative fluid flow path between said fluid inlet and said drain, said alternative fluid flow path including at least a portion of said fluid region and not including said analyzer; and, a venting fluid conduit extending between a source of venting fluid and alternately said fluid region or said interior chamber when said coupler receives said calibration vessel.

8. Analysis apparatus according to claim 7 wherein said alternative fluid flow path is blocked to fluid flow when said coupler receives said calibration vessel.

9. Analysis apparatus according to claim 7 wherein said alternative fluid flow path is not blocked to fluid flow when said coupler receives said calibration vessel.

10. Analysis apparatus according to claim 7 wherein said venting fluid conduit is a second needle having a hollow interior, an inlet end external to said fluid region, and an outlet end alternately in said fluid region or in said interior chamber when said coupler receives said calibration vessel.

11. Analysis apparatus according to claim 4 further comprising a second needle having a hollow interior, an inlet end external to said fluid region, and an outlet end such that said outlet end of said second needle pierces said membrane and extends into said interior chamber of said calibration vessel when the calibration vessel is received by said coupler so as to establish a venting fluid flow path from the source of venting fluid seriatim through said inlet end of said second needle, said hollow interior of said second needle, said outlet end of said second needle into said interior chamber.

12. A liquid sampling system for alternately drawing a testing sample from a flowing liquid stream for analysis by an analyzer during a sampling cycle or for periodically drawing a reference sample for calibration of the analyzer during a calibration cycle, wherein said testing sample and said reference sample are flowed to said analyzer along identical flow paths during said respective sampling and calibration cycles, said system comprising:

a chamber for containing a stream of a first liquid, said chamber including a liquid entrance, a liquid exit, and a first flow path between said entrance and exit;

a hollow, open-ended sampling tube coupled to the chamber such that an inlet end of said sampling tube is in said first flow path inside the chamber and an outlet end of said sampling tube is outside said chamber;

an analyzer for analyzing a liquid sample, said analyzer being coupled to the outlet end of the sampling tube so as to establish a second flow path for said first liquid from the inlet of the sampling tube along said second flow path to the analyzer; and, a coupling member for alternately coupling a container containing a second liquid to said sampling tube without moving said sampling tube such that said inlet end of said sampling tube is immersed in said second liquid whereby said second liquid can flow along said second flow path to said analyzer when said container is coupled to said sampling tube.

13. A liquid sampling system according to claim 12 further comprising a venting fluid conduit extending between a source of venting fluid and said chamber.

14. A liquid sampling system according to claim 13 wherein said venting fluid conduit is a second tube having a hollow interior, an inlet end external to said chamber, and an outlet end in said chamber.

15. A liquid sampling system according to claim 14 further wherein said outlet end of said second tube extends into said container when the container is received by said coupling member so as to establish a venting fluid flow path from the source of venting fluid seriatim through said inlet end of said second tube, said hollow interior of said second tube, said outlet end of said second tube, into said container.

16. An apparatus for alternately drawing a testing sample from a flowing liquid stream for analysis by an analyzer during a sampling cycle or for periodically drawing a reference sample from a standard liquid for calibration of the analyzer during a calibration cycle, further wherein said testing sample and said reference sample are flowed to said analyzer along identical flow paths during said respective sampling and calibration cycles, said apparatus comprising:

(a) a first container for containing at least a portion of said flowing liquid stream during a sampling cycle, said first container including a first liquid entrance and a first liquid exit whereby said flowing liquid stream can be flowed into, through, and out of said first container;

(b) a second container for containing said standard liquid;

(c) a hollow sampling needle having first and second needle ends and first and second needle apertures respectively in said first and second needle ends, further wherein said second needle aperture is in fluid communication with an analyzer inlet conduit; and (d) at least a coupling for coupling said sampling needle to said first container during a sampling cycle whereby said first needle end is immersed in said flowing liquid stream and a testing sample is flowed through said sampling needle to said analyzer inlet conduit, and for coupling said sampling needle to said second container during a calibration cycle without moving said sampling needle whereby said first needle end is immersed in said standard liquid and a reference sample is flowed through said sampling needle to said analyzer inlet conduit.

17. An apparatus for supplying to an analyzer a portion of a primary fluid stream continuously diverted from a primary fluid flow path and, alternately, supplying a known fluid of known composition and concentration to the analyzer, said apparatus comprising:

a housing which houses a sampling chamber and a hollow sampling needle; said housing having an inlet and an outlet, whereby said primary fluid stream can be directed along a primary fluid flow path through said sampling chamber from inlet to outlet; said hollow sampling needle having an inlet in said primary fluid flow path inside said sampling chamber and an outlet in fluid communication with the analyzer, whereby a portion of said primary fluid stream is continuously diverted to the analyzer along a communication path between said analyzer and said primary fluid flow path; said housing being capable of housing alternately a container of said known fluid, whereby said sampling needle inlet can be inserted into said known fluid causing said known fluid, instead of fluid from the primary fluid stream, to be diverted to the analyzer along the same communication path used by said diverted portion of said primary fluid stream.

18. An apparatus according to claim 17 further comprising means for introducing replacement fluid to the container containing the known fluid as fluid flows from the container to the analyzer, so that a vacuum is prevented from forming in the container.

19. An apparatus according to claim 17 further comprising said analyzer, which is connected to said communication path and also to a discharge conduit such that the analyzer is in fluid communication with said primary fluid flow path downstream of said sampling chamber, whereby all of the fluid will be commingled.

20. An apparatus according to claim 17 further comprising said container of said known fluid, said container having a mouth sealed by a frangible seal that can be pierced by said sampling needle to position said sampling needle inlet inside the container within the known fluid.

21. An apparatus according to claim 17 wherein said housing comprises a vial receptacle for housing alternately said container of said known fluid.

22. An apparatus according to claim 21 further comprising a housing cover for covering said vial receptacle when said primary fluid stream is directed through the housing and which cover is removable to expose the vial receptacle when said housing is used to house alternately said container of said known fluid.

23. An apparatus comprising: a housing which houses a sampling chamber, the chamber having an upper portion and a lower portion at a level lower than the upper portion, said housing having a fluid stream inlet for flowing a primary fluid stream into said sampling chamber and a fluid stream outlet for flowing said primary fluid stream out of said sampling chamber; a first hollow needle positioned in said sampling chamber, the first hollow needle having a fluid opening positioned in said lower portion; and an analyzer, the first hollow needle being in fluid communication with the analyzer, whereby the first hollow needle diverts a portion of the primary fluid stream from said sampling chamber to the analyzer.

24. An apparatus according to claims 23 further comprising a discharge conduit from said analyzer by which said analyzer is in fluid communication with the flow path of said primary fluid stream downstream of said sampling chamber whereby all of the fluid will be commingled.

25. An apparatus according to claim 23 wherein said housing further comprises a vial receptacle for housing alternately a container of a known fluid of known composition and concentration whereby said fluid opening of the first hollow needle can be inserted into said known fluid causing said known fluid, instead of fluid from the primary fluid stream, to be diverted to the analyzer along the same communication path used by said diverted portion of said primary fluid stream.

26. An apparatus according to claim 25 further comprising said container of said known fluid, said container having a mouth sealed by a frangible seal that can be pierced by the first hollow needle to position the fluid opening of said first hollow needle inside the container within the known fluid.

27. An apparatus according to claim 25 further comprising a housing cover for covering said vial receptacle when said primary fluid stream is directed through the housing and which is removed to expose the vial receptacle when said vial receptacle is used to house alternately said container of said known fluid.

28. An apparatus according to claim 26 further comprising means for supplying replacement fluid to the container containing the known fluid as fluid flows from the container to the analyzer, so that a vacuum is prevented from forming in the container.

* * * * *